United States Patent [19]

Kuwana et al.

[11] Patent Number: 5,056,354
[45] Date of Patent: Oct. 15, 1991

[54] ROAD CONDITION MONITORING SYSTEM

[75] Inventors: Kazutaka Kuwana, Toyota; Kuniaki Okamoto, Nagoya; Tsuyoshi Yoshida, Obu; Hiroyuki Ichikawa, Okazaki; Masaru Kamikado, Anjo; Nobuyasu Nakanishi, Toyota; Tatsuo Sugitani, Mishima; Kazunori Sakai, Aichi, all of Japan

[73] Assignees: Aisin Seiki K.K.; Toyota Jidosha K.K., both of Aichi, Japan

[21] Appl. No.: 563,158

[22] Filed: Aug. 6, 1990

[30] Foreign Application Priority Data

Aug. 4, 1989 [JP] Japan .................................. 1-203491

[51] Int. Cl.⁵ .......................................... G01N 19/02
[52] U.S. Cl. ............................................ 73/9; 73/146
[58] Field of Search ............................ 73/9, 8, 146, 7; 364/426.02

[56] References Cited

U.S. PATENT DOCUMENTS 4,387,587 6/1983 Faulconer .................. 73/9
4,958,512 9/1990 Johnsen .................... 73/146

FOREIGN PATENT DOCUMENTS 5474983 11/1977 Japan .

Primary Examiner—Donald O. Woodiel
Attorney, Agent, or Firm—Sughrue, Mion, Zinn, Macpeak & Seas

[57] ABSTRACT

The invention is directed to an arrangement for monitoring a road condition which determines the coefficient of friction of the road surface on the basis of a signal corresponding to an acceleration of a vehicle detected by an acceleration sensor. The signal is converted into one of at least two predetermined values by conversion means in response to a magnitude of the acceleration every cycle of a predetermined time period. The converted value is summed up by summing means by a predetermined number of consecutive cycles to provide a total value in the last cycle thereof which is stored in memory means. Then, in determination means, one of at least two standard values is selected in response to the condition of increase or decrease of the total value in the present cycle provided by the summing means as compared with the total value in the previous cycle stored in the memory means. And, the total value in the present cycle is compared with the above one of at least two standard values to produce a road condition signal corresponding to a result of comparison which represents the coefficient of friction of the road surface. The present system is applicable to an anti-skid control system for an automotive vehicle.

6 Claims, 7 Drawing Sheets

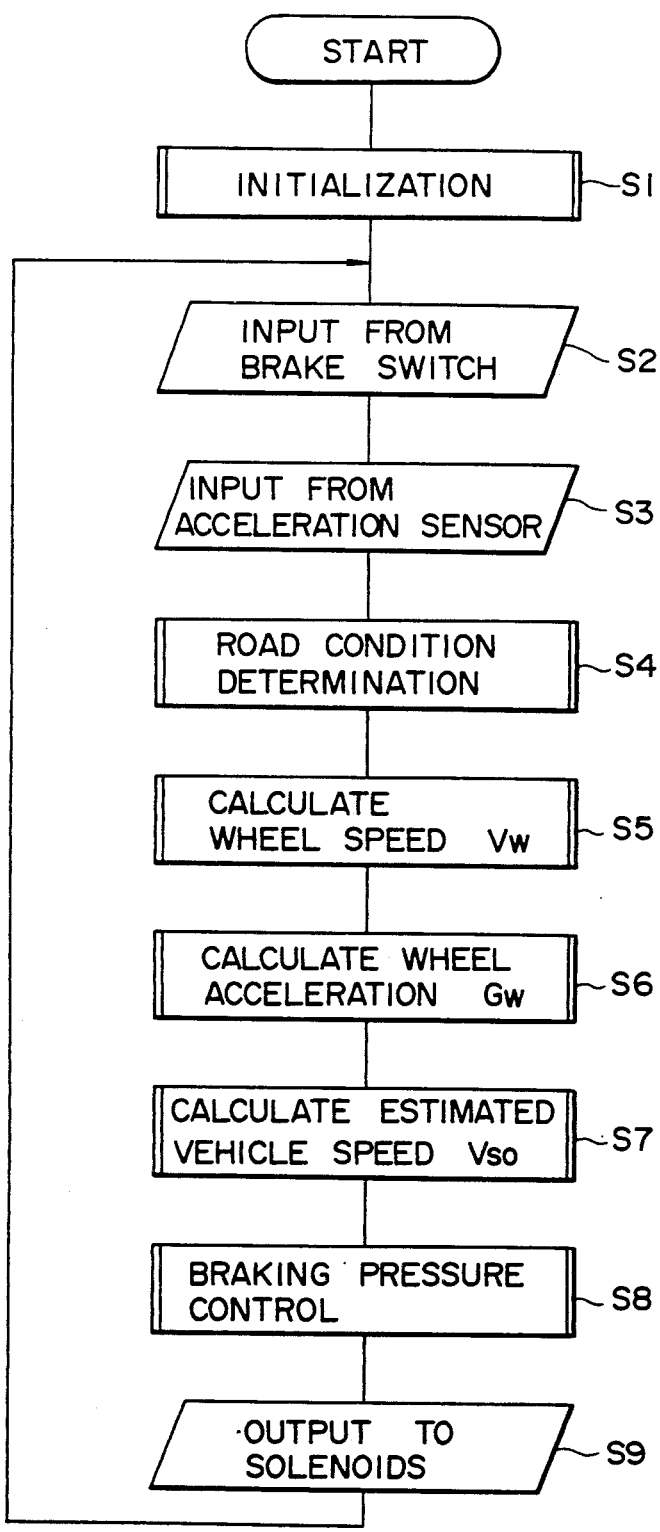

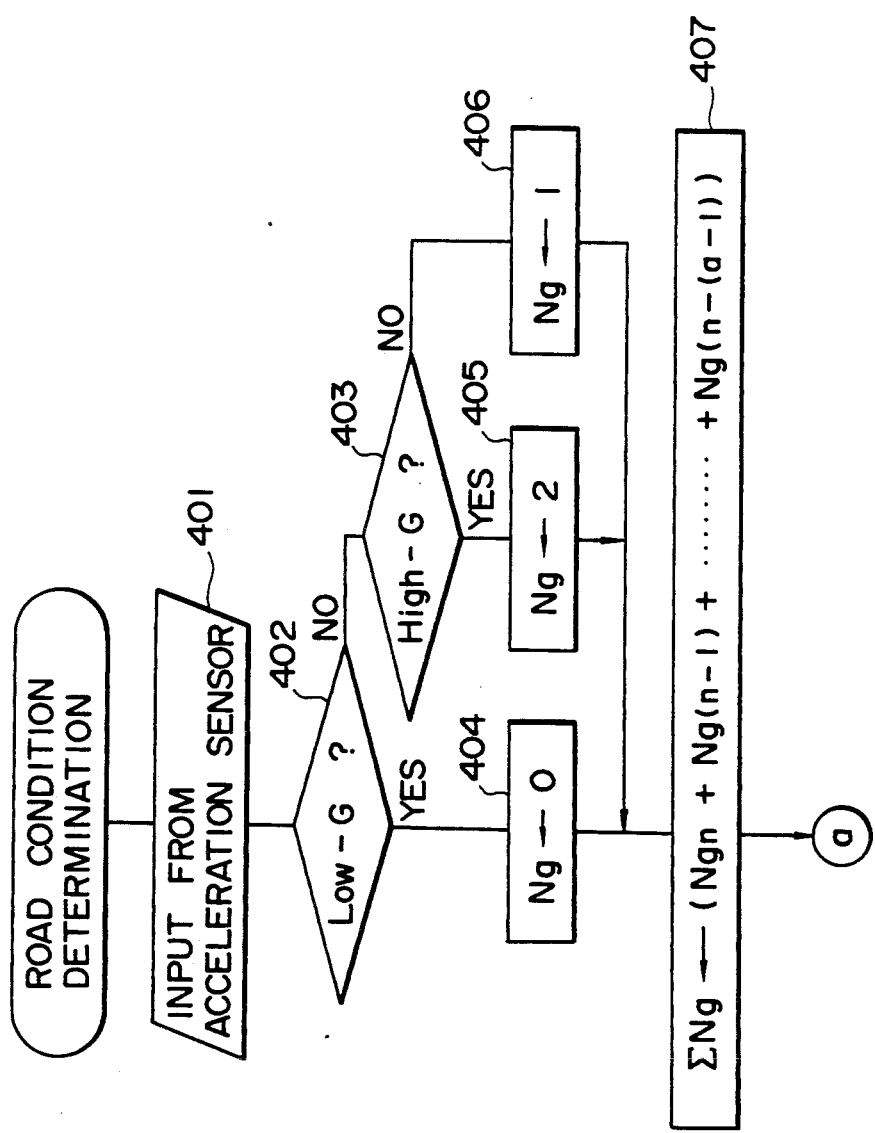

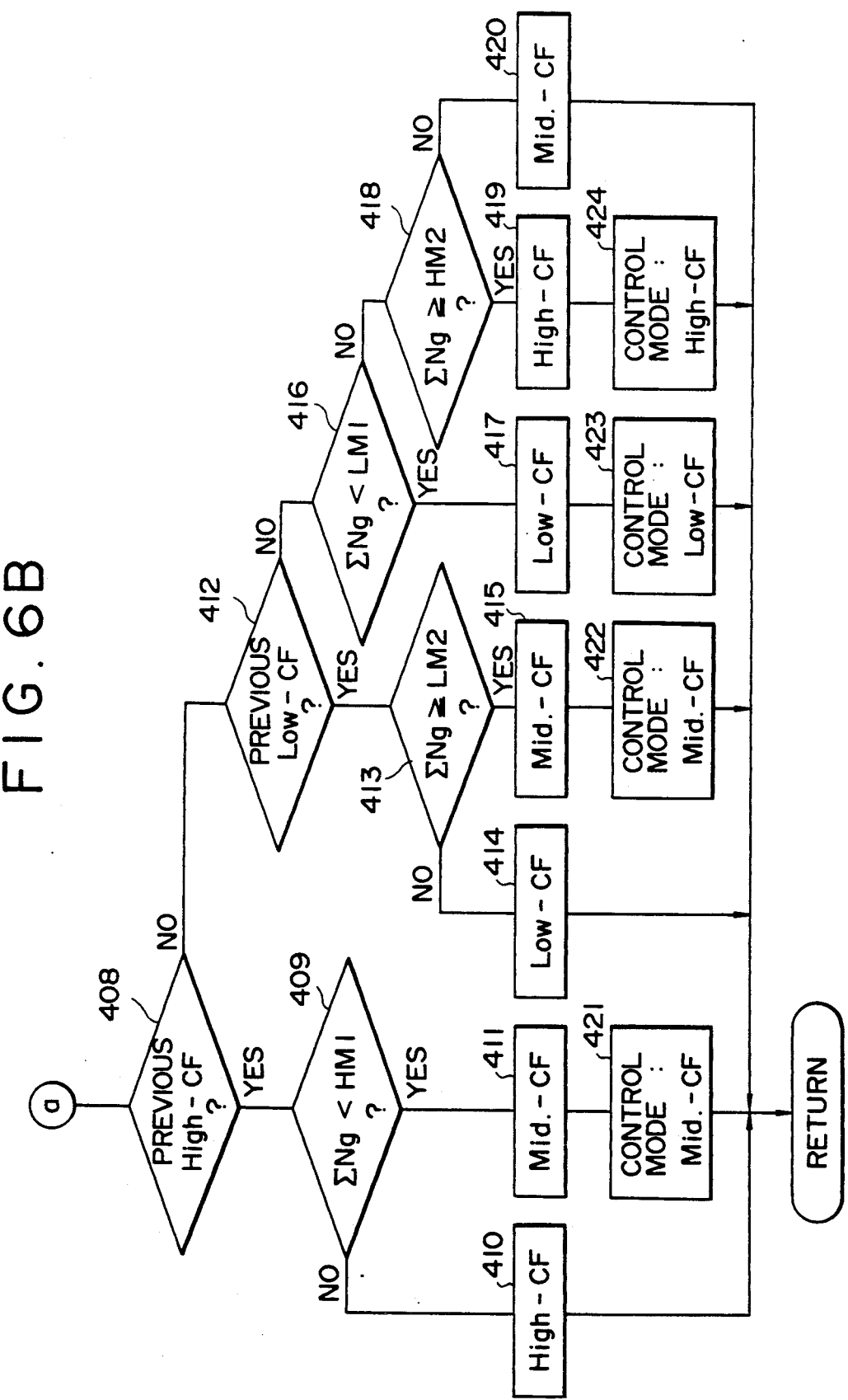

ROAD CONDITION MONITORING SYSTEM

BACKGROUND OF THE INVENTION

1. Field of the Invention

The present invention relates to a road condition monitoring system, and more particularly to the system for determining a coefficient of friction of the road surface, which is applicable to an anti-skid control system for controlling braking force applied to road wheels in braking operation to prevent the road wheels from being locked.

2. Description of the Prior Art

It is known that the vehicle stability or the controllability is influenced detrimentally by the road surface condition, when road wheels are locked in abrupt braking operation. In order to prevent the road wheels from being locked, therefore, there has been employed an anti-skid control system which controls the braking force by decreasing, increasing, or holding a hydraulic braking pressure supplied to a wheel brake cylinder, and which is also called as an anti-locking control system. In view of the fact that when the hydraulic braking pressure supplied to the wheel brake cylinder is increased, the rotational speed of the road wheel is rapidly reduced immediately before the coefficient of friction of the road surface relative to the road wheel reaches its maximum value, the anti-skid control system controls the wheel cylinder pressure according to the deceleration of the vehicle in order that a slip rate of the road wheel results in around 20%, that is, the maximum coefficient of friction is obtained.

The above-described coefficient of friction of the road surface varies according to the type of the road wheel, the condition of the road surface and other factors. Especially, it is much influenced by the condition of the road surface, such as dry or wet road surface. Therefore, the coefficient of friction (hereinafter, simply referred to as CF) of the road surface is a very important factor for the anti-skid control, and it is necessary to control the braking force in response to the CF of the road surface in order to raise the efficiency of the braking operation with the stability of the vehicle maintained. Although it is impossible to detect directly the CF of the road surface on the running vehicle, it is possible to estimate the CF of the road surface from the deceleration of the vehicle in its braking operation, so that an acceleration sensor is employed as disclosed in Japanese Patent Laid-open Publication No. 54-74983. Accordingly, the output of the acceleration sensor is provided for estimating the vehicle speed, or changing a speed or quantity of the brake fluid during the control of increase or decrease of the hydraulic braking pressure. In terms of the acceleration mentioned above, the deceleration is included therein, and when the terminology of the acceleration is employed, the deceleration will be included therein unless otherwise defined, hereinafter.

As for the acceleration sensor, various sensors are known such as a mercury switch, or those using a moving-coil, a pendulum, piezoelectric or photoelectric elements. However, when these are installed on a vehicle to detect the deceleration thereof, the output of the acceleration sensor may not correspond to the deceleration of the vehicle due to a vehicle vibration, for example, Therefore, in the case where the output of the acceleration sensor indicates a high acceleration (hereinafter referred to as High-G) or a low acceleration (hereinafter referred to as Low-G), if the CF of the road surface is determined corresponding directly to the above outputs, a hydraulic braking pressure will be increased to cause the lock of the road wheel when the vehicle is running on a road of a low coefficient of friction (hereinafter referred to as Low-CF), or a hydraulic braking pressure will be so much decreased to increase the braking distance when the vehicle is running on a road of a high coefficient of friction (hereinafter referred to as High-CF).

In Japanese Patent Laid-open Publication No. 54-74983, it is proposed that a predetermined delay of time is to be provided in the anti-skid control for changing the High-CF mode thereof to the Low-CF mode thereof, whereas no delay of time is to be provided in the control for changing the Low-CF mode to the High-CF mode. And, it is proposed in Japanese Utility model Laid-open Publication No. 64-21056 that the anti-skid control is changed to the control for the road of High-CF or that for the road of Low-CF in case of detecting the High-G or Low-G respectively.

However, either system disclosed in the above publications will cause the lock of the road wheel in braking operation on a rough road with continuing uneven ground of Low-CF such as that of a pressed snow road. This is because, according to the art disclosed in the former publication, when intermittent High-G inputs are caused by the uneven road with a period shorter than the delay time in changing from the High-CF mode to the Low-CF mode, the anti-skid control is fixed to that in the High-CF mode, also because, according to the art disclosed in the latter publication, the High-CF mode is selected for the rough road irrespective of the actual CF of the road surface.

FIG. 9 shows the anti-skid control operation of the above prior art when the acceleration detected by the acceleration sensor on the rough Low-CF road varies as shown in (A). In the case where the detected acceleration vibrates as shown in (A), if the period of High-G is shorter than the delay time in changing from the High-CF mode to the Low-CF mode, the result of determination of the road condition is fixed to the High-CF mode as shown in (B). Or, it is fixed to the High-CF mode due to the rough road. Consequently, in the estimated vehicle speed set in accordance with the wheel speed and the CF of the road surface, the estimated vehicle speed Vso calculated according to the High-CF mode is set to be lower than the actual estimated vehicle speed to be set at the time of the Low-CF mode as shown in a phantom line in (C), so that the difference between those estimated vehicle speeds becomes large when the wheel speed Vw is decreased, and resultantly the lock of the wheel is caused as shown at the right side of (C).

SUMMARY OF THE INVENTION

Accordingly, it is an object of the present invention to provide a road condition monitoring system which enables to output a signal representing a road condition in response to a coefficient of friction of the road surface even on a rough road of a low coefficient of friction.

In accomplishing the above and other objects, a road condition monitoring system comprises an acceleration sensor for detecting an acceleration of a vehicle and producing a signal corresponding thereto, conversion means for receiving the signal from the acceleration sensor and converting the signal into one of at least two predetermined values in response to a magnitude of the acceleration every cycle of a predetermined time period, summing means for summing up the above one of at least two predetermined values in a predetermined number of consecutive cycles to provide a total value in the last cycle thereof, memory means for storing the total value provided by the summing means, and determination means for selecting one of at least two standard values in response to the condition of increase or decrease of the total value in the present cycle as compared with the total value in the previous cycle, and comparing the total value in the present cycle with the above one of at least two standard values to produce a road condition signal corresponding to a result of comparison.

BRIEF DESCRIPTION OF THE DRAWINGS

The above stated objects and following description will become readily apparent with reference to the accompanying drawings, wherein like reference numerals denote like elements, and in which:

FIG. 5 is a flowchart showing the operation of the main routine for the braking force control of the electronic controller according to an embodiment of the present invention;

FIG. 6 consists of FIGS. 6A and 6B which form a flowchart showing the operation of the sub-routine for determining the coefficient of friction of the road surface;

DESCRIPTION OF THE PREFERRED EMBODIMENTS

Figure 1:
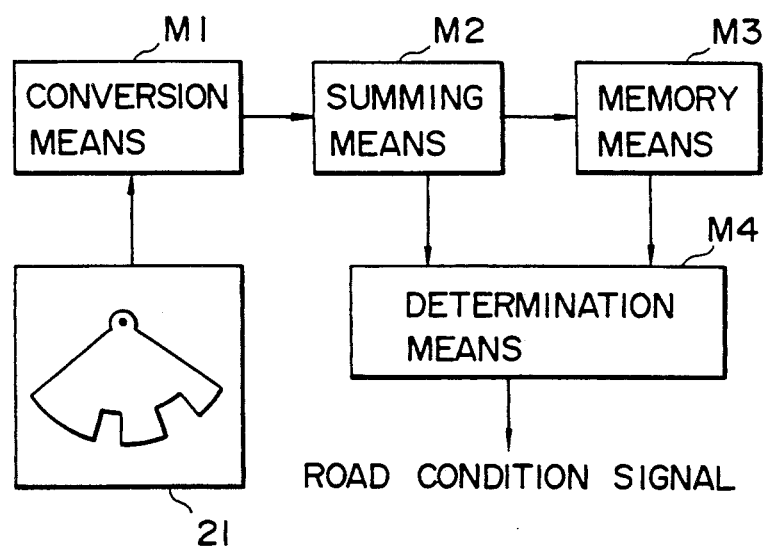
FIG. 1 is a general block diagram illustrating a road condition monitoring system according to the present invention.

Referring to FIG. 1, there is schematically illustrated a road condition monitoring system according to the present invention incorporated into an anti-skid control system. In this road condition monitoring system, there is provided with an acceleration sensor 21 which detects an acceleration of a vehicle and produces a signal corresponding thereto. This signal is fed to conversion means M1 which converts the signal into one of at least two predetermined values in response to a magnitude of the acceleration every cycle of a predetermined time period. Then, summing means M2 sums up the above one of at least two predetermined values in a predetermined number of consecutive cycles, e.g., 12 consecutive cycles and provides a total value in the last cycle thereof which is stored in memory means M3.

Determination means M4 receives from the summing means M2 the total value in the present cycle and also receives the total value in the previous cycle stored in the memory means M3. Then, the determination means M4 selects one of at least two standard values, e.g., high and low standard values, in response to the condition of increase or decrease of the total value in the present cycle as compared with the total value in the previous cycle. For instance, when the total value in the present cycle increases comparing with that in the previous cycle, the high standard value is selected, whereas the low standard value is selected when the total value in the present cycle decreases, so that a hysteresis characteristic is provided. The determination means M4 compares the total value in the present cycle with the above one of at least two standard values to produce a road condition signal corresponding to a result of comparison, e.g., a signal representing a high coefficient of friction of the road surface, or a signal representing a low coefficient of friction of the road surface.

Figure 2:
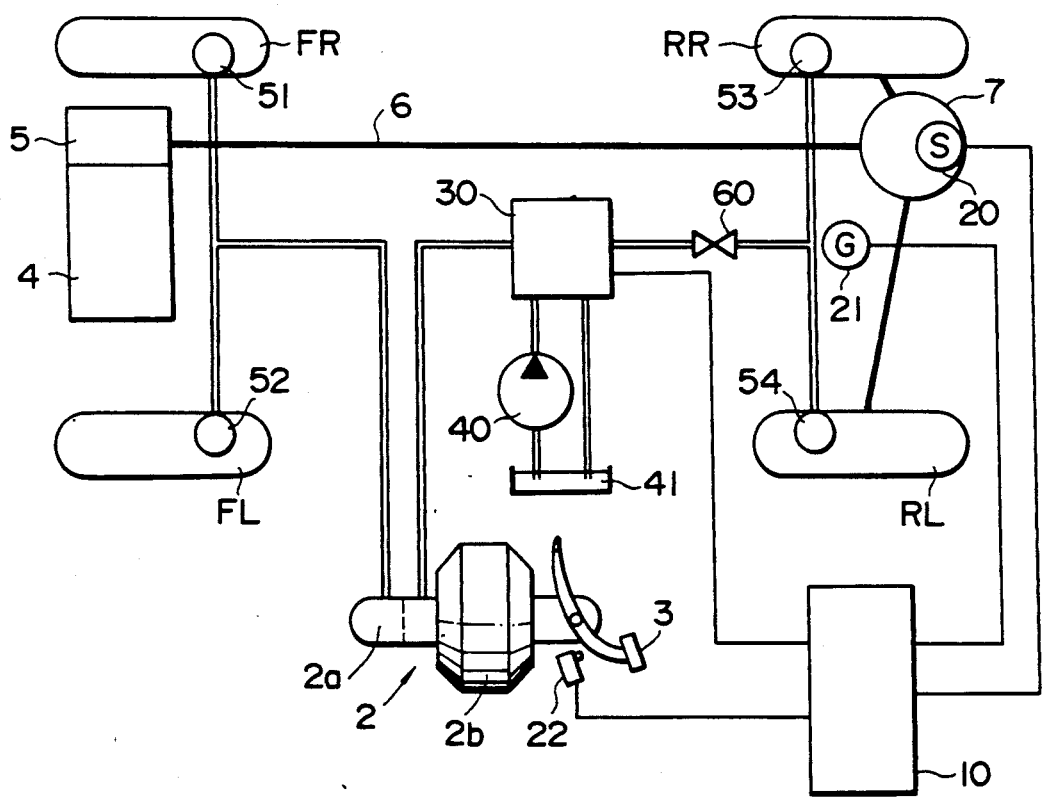
FIG. 2 is a schematic block diagram of an anti-skid control system having a road condition monitoring system of an embodiment of the present invention.

More specifically, an embodiment of the present invention is illustrated in FIGS. 2 to 6. Referring to FIG. 2, there is illustrated a vehicle having an anti-skid apparatus which includes a hydraulic pressure generator 2, comprising a master cylinder 2a and a booster 2b operated in response to depression of a brake pedal 3. The master cylinder 2a of a so-called tandem-type directly connected to wheel brake cylinders 51, 52 of road wheels FR, FL, and connected to wheel brake cylinders 53, 54 of road wheels RR, RL via an actuator 30 and a proportioning valve 60. The road wheel FR designates a road wheel at the fore right side as viewed from the position of a driver's seat, the road wheel FL designates a road wheel at the fore left side, the road wheel RR designates a road wheel at the rear right side, and the road wheel RL designates a road wheel at the rear left side. In the present embodiment, a front and rear dual circuits system for braking front and rear road wheels independently is employed as is apparent from FIG. 2. An internal combustion engine 4 mounted on the vehicle according to the present embodiment is connected to a transmission 5 of a well known type which is connected to a differential gear 7 through a propeller shaft 6. The differential gear 7 is connected to the road wheels RR, RL, so that a driving power of the engine 4 is transmitted thereto.

When the brake pedal 3 is depressed, the booster 2b is operated in response to depression of the brake pedal 3, so that the master cylinder 2a is boosted by the booster 2b. Consequently, a hydraulic braking pressure is discharged from the master cylinder 2a in response to depression of the brake pedal 3 and applied to the wheel brake cylinders 51 to 54. When the hydraulic braking pressure is applied to the wheel brake cylinders 51, 52, the road wheels FR, FL or non-driven road wheels are braked, and when it is applied to the wheel brake cylinders 53, 54, the road wheels RR, RL or driven road wheels are braked.

Figure 3:
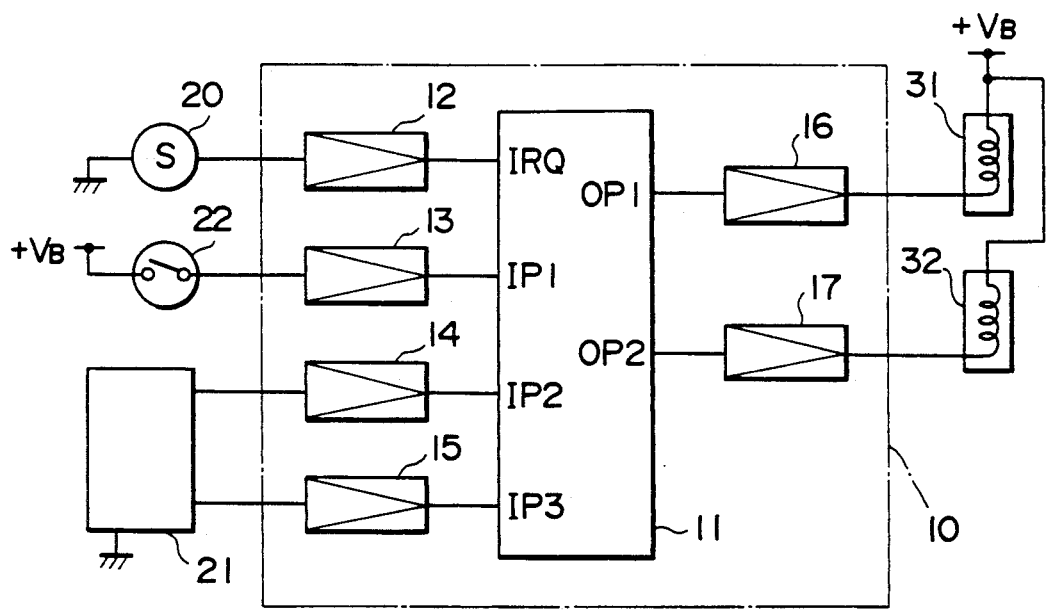
FIG. 3 is a block diagram illustrating the arrangement of the electronic controller shown in FIG. 2.

The actuator 30 is disposed between the master cylinder 2a and the wheel brake cylinders 53, 54, and connected to a pump 40 and a reservoir 41. The pump 40 is driven by the engine 4, so that the pressure of the brake fluid in the reservoir 41 is raised and supplied to the actuator 30 as a power pressure. The actuator 30 is provided with a pair of solenoid valves (not shown) having solenoids 31, 32 respectively as shown in FIG. 3 which are energized or de-energized in response to outputs from an electronic controller 10. Then, an appropriate control mode is selected from such hydraulic pressure control modes as an "increase mode" where the hydraulic braking pressure in each of the wheel brake cylinders 53, 54 is increased when the hydraulic pressure discharged from the pump 40 is supplied thereto, a 'decrease mode" where the hydraulic braking pressure is decreased when each of the wheel brake cylinders 53, 54 is communicated with the reservoir 41, and a "hold mode" where the hydraulic braking pressure is held as it is, so that the hydraulic braking pressure is controlled to prevent the road wheels RR, RL from being locked. Further, there is provided a 'direct mode" where the master cylinder 2a is directly communicated with the wheel brake cylinders 53, 54.

Between the actuator 30 and the wheel brake cylinders 53, 54, there is disposed a proportioning valve 60 which decreases the hydraulic braking pressure applied to the rear wheel brake cylinders 53, 54 at a certain rate of the input hydraulic pressure to form an approximate ideal braking force distribution. In this embodiment, employed is a so called load-sensing type proportioning valve whose characteristic varies according to a supporting load at the road wheels RR, RL. At the differential gear 7 connected to the road wheels RR, RL, there is disposed a wheel speed sensor 20 by which a rotational speed of the propeller shaft 6, i.e., a wheel speed Vw of an average of the wheel speeds of the road wheels RR, RL is detected, so that a signal corresponding to the wheel speed Vw is fed to the electronic controller 10.

Figure 4:
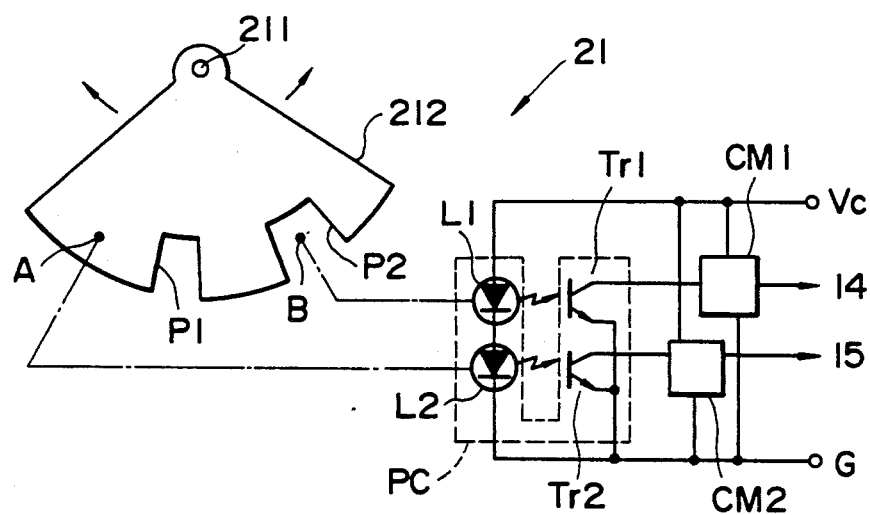
FIG. 4 is a schematic drawing of an acceleration sensor shown in FIG. 2.

At an appropriate position of the vehicle to which a vibration from the engine 4 or the road is hardly transmitted, there is fixed an acceleration sensor 21 which detects an acceleration of the vehicle and outputs in response thereto electric signals to the electronic controller 10. The acceleration sensor 21 in this embodiment is a photoelectric sensor as shown in FIG. 4, which includes a fan-shaped pendulum 212 rotatably mounted around an axis 211, a photocoupler PC disposed opposite to the pendulum 212 and a circuit element connected to the photocoupler PC. The pendulum 212 is formed with slits P1, P2 for allowing light pass therethrough at its peripheral end portion. The photocoupler PC is disposed in such a place where light emitting diodes L1, L2 are positioned at points A and B opposite to the peripheral end portion of the pendulum 212 as shown in FIG. 4. The photocoupler PC comprises the light emitting diodes L1, L2 and phototransistors Tr1, Tr2 positioned opposite thereto respectively, between which the peripheral end portion of the pendulum 212 is arranged to be positioned. Then, a voltage signal at high level (H) or low level (L) is output from each of comparators CM1, CM2 in response to the positions of the slits P1, P2 of the pendulum 212 relative to the light emitting diodes L1, L2.

Referring back to FIG. 2, there is provided with a brake switch 22 which is opened or closed in response to operation of the brake pedal 3. When the brake pedal 3 is depressed, the brake switch 22 is turned on, so that a stop lamp (not shown) is lighted and at the same time an electric signal indicating the depression of the brake pedal 3 is fed to the electronic controller 10. As shown in FIG. 3, the electronic controller 10 is provided with a microprocessor 11, a waveform shaping circuit 12, input buffers 13, 14, 15 and output buffers 16, 17. As for the microprocessor 11 in this embodiment, employed is an one-chip microcomputer on the market including a central processing unit or CPU, a read-only memory or ROM for storing a program and a random access memory or RAM for reading and writing data to perform the program, which are connected with input ports and output ports via a common bus to execute the input-/output operations relative to external circuits. The signal detected by the wheel speed sensor 20 is fed to the waveform shaping circuit 12 where the signal is converted into a square wave and fed to an interruption port IRQ of the microprocessor 11. Thus, the microprocessor 11 is interrupted with a time interval which is determined in response to the wheel speed detected by the wheel speed sensor 20. The output signal of the brake switch 22 is fed to an input port IP1 through the input buffer 13 in the form of a high level (H) signal when the brake switch 22 is turned on, or a low level (L) signal when it is turned off. Further, the output signals of the acceleration sensor 21 are fed to input ports IP2, IP3 of the microprocessor 11 through the input buffers 14, 15. That is, the output signals at high level (H) or low level (L) are fed to the input ports IP2, IP3 in response to the acceleration of the vehicle. An output port OP1 of the microprocessor 11 is connected to the solenoid 31 for one of the electromagnetic valves in the actuator 30 through the output buffer 16. An output port OP2 is connected to the solenoid 32 for the other of the electromagnetic valves through the output buffer 17. The output buffers 16, 17 amplify the electric signals output from the output ports OP1, OP2 to energize the solenoids 31, 32 respectively.

A program routine executed by the electronic controller 10 for the anti-skid control will now be described with reference to flowcharts shown in FIGS. 5 and 6. The program includes a main routine shown in FIG. 5, and an interruption routine shown in FIG. 6 which is performed when an input is fed to the interruption port IRQ. The program routine starts when a power source to the electronic controller 10 is turned on, and provides for initialization of the system at Step S1, wherein outputs of the output ports OP1, OP2 are arranged to de-energize the solenoid 31, 32. Then, the program proceeds to Step S2 where the signal indicating the condition of the brake switch 22 is fed to the microprocessor 11. Next, the program proceeds to Step S3 where the electric signals are fed to the microprocessor 11 through the input buffers 14, 15 in response to the vehicle acceleration detected by the acceleration sensor 21. Then, the determination of the road condition or the coefficient of friction of the road surface is executed on the basis of the signals fed from the acceleration sensor 21 at Step S4 which will be described later in detail with reference to the subroutine shown in FIG. 6.

The program proceeds further to Step S5 where an average wheel speed Vw of the rear road wheels RR, RL is calculated on the basis or a period $\Delta Tw$ of the signal output from the wheel speed sensor 20, in accordance with the following equation:

$$Vw = K/\Delta Tw \qquad (1)$$

where K is a constant which is set according to the characteristics of the wheel speed sensor 20, and the period $\Delta Tw$ is obtained through the interruption routine which is executed separately. Then, at Step S6, a wheel acceleration Gw of the rear road wheels RR, RL is calculated on the basis of the wheel speed Vw calculated at Step S5, in accordance with the following equations (2) and (3):

$$Int = (\Delta Tw(n) + \Delta Tw(n-1))/2 \quad (2)$$

$$Gw(n) = (Vw(n) - Vw(n-1))/Int \quad (3)$$

where "Int" corresponds to a time interval of the interruption, Vw(n) and ΔTw(n) respectively correspond to the wheel speed and the time period obtained in the present cycle of the routine, while Vw(n−1) and ΔTw(n−1) respectively correspond to the wheel speed and the period obtained in the previous cycle of the routine.

Accordingly, an estimated vehicle speed Vso is calculated at Step S7, on the basis of the wheel speed Vw calculated at Step S5, the condition of the brake switch 22 input at Step S2 and the road condition determined at Step S4. The program proceeds to Step S8 where it is determined how the hydraulic braking pressure in the wheel brake cylinders 53, 54 is regulated according to the wheel speed Vw, the wheel acceleration Gw and the estimated vehicle speed Vso obtained at Steps S5, S6 and S7 respectively. The program then proceeds to Step S9 where signals for driving the solenoids 31, 32 in response to the result determined at Step S8 are output from the output ports OP1, OP2, so that the hydraulic braking pressure is increased, decreased or held in response to the result. The above-described Steps S1 to S9 are repeatedly executed. In the case where the slip rates to the road surface of the road wheels RR, RL are large with the wheel speed Vw decreased rapidly, the hydraulic braking pressure is decreased to rotate the road wheels RR, RL, so that the road wheels RR, RL are prevented from being locked.

Next will be described the determination of the road condition executed at Step S4 during the anti-skid control operation with reference to FIGS. 6A and 6B. Initially, the output signal of the acceleration sensor 21 is fed to the microprocessor 11 at Step 401, and determined at Steps 402 and 403 to set a predetermined value Ng. That is, the output signal corresponding to the acceleration detected by the acceleration sensor 21 is converted into the value Ng as follows:

| Acceleration Sensor Output (Ao) | Value (Ng) |
| --- | --- |
| Low-G    Ao < 0.2G | 0 |
| Mid.-G   0.2G ≦ Ao < 0.4G | 1 |
| High-G   0.4G ≦ Ao | 2 | where each of Low-G, Mid.-G and High-G corresponds to the acceleration value detected by the acceleration sensor 21 in one of the three ranges divided according to their magnitude, and "G" combined with the numerals represents a gravity acceleration.

Accordingly, when the signal fed from the acceleration sensor 21 indicates less than 0.2 G, it is determined to be Low-G at Step 402 and the value Ng is set to be "0". If it indicates 0.2 G or larger, the program proceeds to Step 403 where, if it indicates 0.4 G or larger, the value Ng is set to be "2" at Step 405, otherwise the value Ng is set to be "1" at Step 406. In the microprocessor 11, the above-described determination of the signal fed from the acceleration sensor 21 is executed repeatedly every cycle of a predetermined time period, e.g., 5 milliseconds. Then, the value Ng is summed for a predetermined number of consecutive cycles, e.g., 12 consecutive cycles, and the total value ΣNg is obtained at Step 407, where Ngn corresponds to the value set in response to the signal fed from the acceleration sensor 21 in the present cycle, while Ng(n−1) corresponds to the value set in response to the signal fed in the previous cycle, and Ng(n-a) corresponds to the value set in response to the signal fed in the "a" number of cycles prior to the present cycle.

Figure 7:
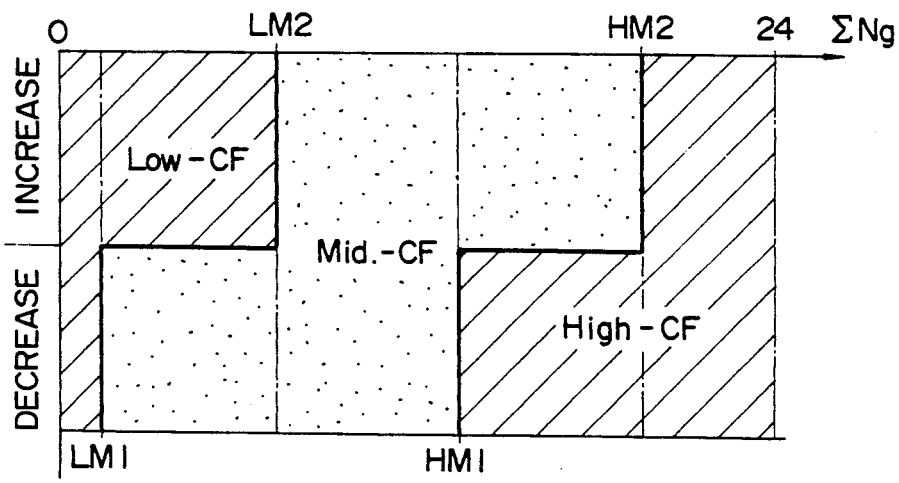
FIG. 7 is a timing chart showing a variation of standard values for use in determining the coefficient of friction of the road surface according to the present embodiment.

On the basis of the total value ΣNg, the determination of the road condition or the coefficient of friction (referred to as CF) of the road surface is performed at Steps following Step 408. The CF of the road surface will be divided into High-CF, Mid.-CF and Low-CF according to the total value ΣNg. In FIG. 7, the abscissa represents the total value ΣNg and the ordinate is divided into two regions, either one of which will be selected according to increase or decrease of the total value ΣNg obtained in the present cycle as compared with that obtained in the previous cycle. That is, in the case where the CF of the road surface is decreased, if it is decreased from Mid.-CF to Low-CF, a first low standard value LM1 is selected, whereas if it is decreased from High-CF to Mid.-CF, then a first high standard value HM1 is selected. In the case where the CF of the road surface is increased, if it is increased from Low-CF to Mid.-CF, a second low standard value LM2 is selected, whereas if it is increased from Mid.-CF to High-CF, a second high standard value HM2 is selected. As shown in FIG. 7, therefore, those standard values are set to be in such relationships as LM1<LM2 and HM1<HM2 to provide a hysteresis characteristic in case of increase or decrease of the CF of the road surface.

At Steps following Step 408 in FIG. 6B, the determination of the CF of the road surface in the present cycle is executed on the basis of the result of determination of the CF of the road surface in the previous cycle and the total value ΣNg in the present cycle. Firstly, if it is determined at Step 408 that the CF of the road surface was High-CF in the previous cycle, the program proceeds to Step 409 where it is determined whether the total value ΣNg is less than the first high standard value HM1 with reference to FIG. 7. If the total value ΣNg is equal to or more than the value HM1, it is affirmed to be High-CF at Step 410. If it is less than the value HM1, the program proceeds to Step 411 where it is determined to be Mid.-CF.

In the case where it is not determined at Step 408 that the CF of the road surface was High-CF in the previous cycle, the program proceeds to Step 412 where it is determined whether the CF of the road surface was Low-CF in the previous cycle. If it is determined that the CF of the road surface was Low-CF in the previous cycle, then the program proceeds to Step 413 where it is determined whether the total value ΣNG is equal to or more than the second low standard value LM2. If it is less than the value LM2, the program proceeds to Step 414 where it is determined to be Low-CF, whereas if it is equal to or more than the value LM2, the program proceeds to Step 415 where it is determined to be Mid.-CF.

On the contrary, in the case where it is not determined at Step 412 that the CF of the road surface was Low-CF in the previous cycle, then it means that the CF of the road surface has been Mid.-CF or High-CF, the program proceeds to Step 416 where it is determined whether the CF of the road surface is less than the first low standard value LM1. If the result is affirmative, the program proceeds to Step 417 where it is determined to be Low-CF, whereas if the result is negative, the program proceeds to Step 418 where it is determined whether the CF of the road surface is equal to or more than the second high standard value HM2. If the result at Step 418 is affirmative, the CF of the road surface is determined to be High-CF at Step 419, whereas if the result is negative, it is determined to be Mid.-CF at Step 420. Consequently, control modes for the anti-skid operation are changed at Steps 421 to 424 in accordance with the result of the determination at Steps 411, 415, 417 and 419, while the results of the determination at Steps 410, 414 and 420 are provided as they are for the operation at Step S7 in the main routine.

Figure 8:
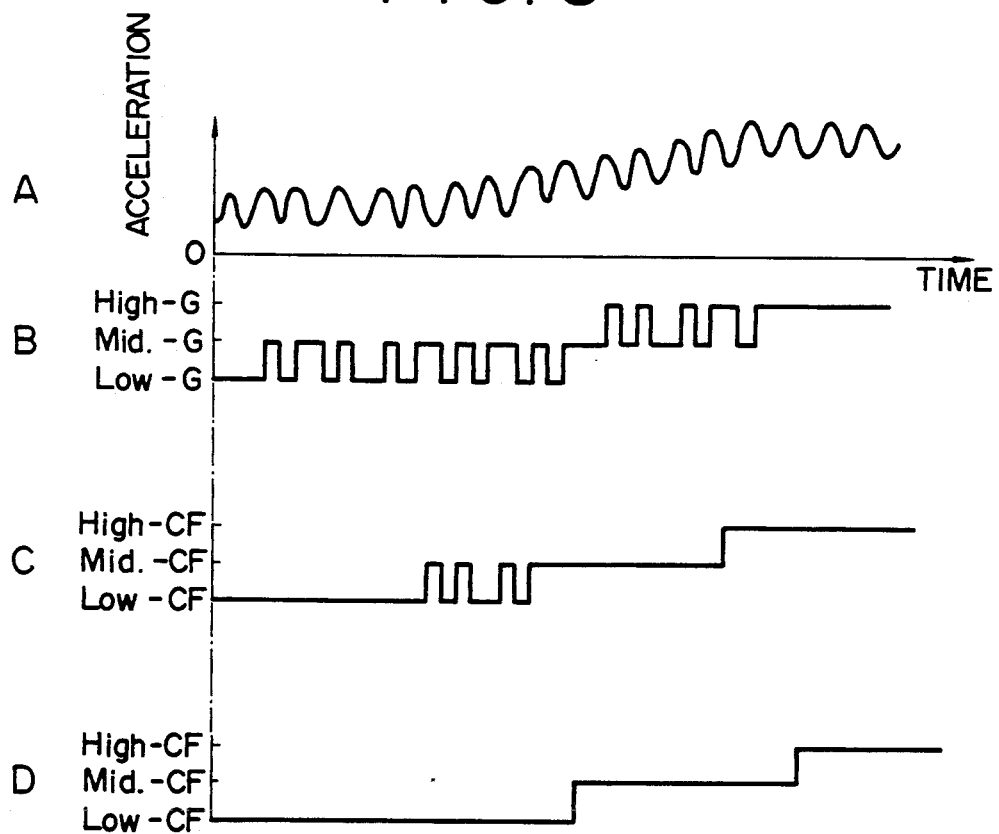
FIG. 8 is a diagram showing the operation in determining the coefficient of friction of the road surface in response to a variation of acceleration detected by the acceleration sensor.
Figure 9:
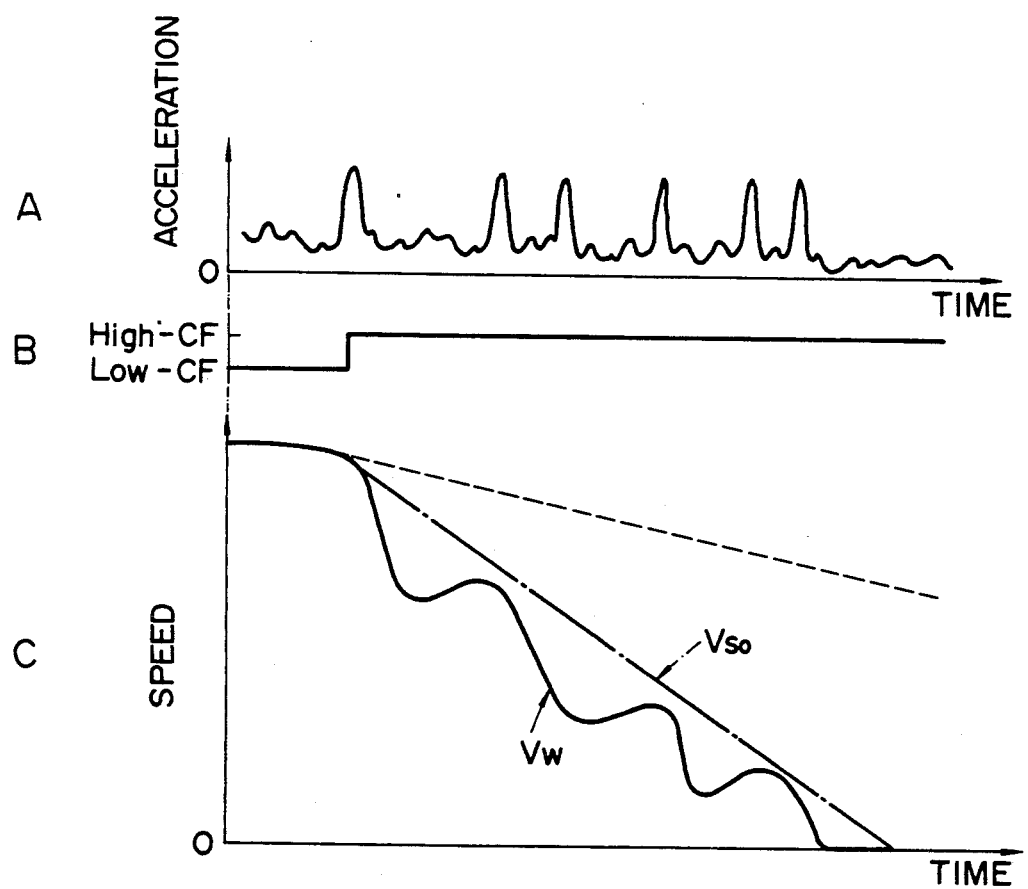
FIG. 9 is a diagram showing the operation of the anti-skid control in response to the variation of acceleration in the prior art.

The operation of the present embodiment in determining the CF of the road surface will be described with reference to FIG. 8 showing timing charts of the vehicle acceleration detected by the acceleration sensor 21 in (A), High-G, Mid.-G and Low-G determined in response to the signal fed from the acceleration sensor 21 in (B), the CF of the road surface determined by comparing the total value ΣNg with fixed high and low standard values in (C), and the CF of the road surface determined by comparing the total value ΣNg with several standard values for providing the hysteresis characteristic as in the present embodiment in (D). In the case where the vehicle acceleration varies from the value at Low-G level to the value at High-G level with noises as shown in (A), the result of determination of High-G, Mid.-G or Low-G by the acceleration sensor 21 varies according to the noises as shown in (B). Therefore, if each of High-G, Mid.-G and Low-G is converted into the corresponding value Ng respectively and the total value ΣNg is calculated to determine the CF of the road surface as described above, the result of the determination is not much influenced by the noises as shown in (C). However, in the case of (C), when the determination of changes between High-CF, Mid.-CF and Low-CF is executed, the fixed standard values are employed without providing the hysteresis characteristic, so that the result is likely influenced by the noises. In the above-described preferred embodiment, therefore, the standard values to be compared with the total value ΣNg are set to provide the hysteresis characteristic, so that the result of determination of the CF of the road surface will be stable without being influenced by the noises. Accordingly, an appropriate signal corresponding to the CF of the road surface may be output even on the rough road with the low coefficient of friction.

It should be apparent to one skilled in the art that the above-described embodiments are merely illustrative of but a few of the many possible specific embodiments of the present invention. Numerous and various other arrangements can be readily devised by those skilled in the art without departing from the spirit and scope of the invention as defined in the following claims.

What is claimed is:

1. A road condition monitoring system comprising:
   an acceleration sensor for detecting an acceleration of a vehicle and producing a signal corresponding thereto;
   conversion means for receiving said signal from said acceleration sensor and converting said signal into one of at least two predetermined values in response to a magnitude of said acceleration every cycle of a predetermined time period;
   summing means for summing up said one of at least two predetermined values in a predetermined number of consecutive cycles to provide a total value in the last cycle thereof;
   memory means for storing the total value provided by said summing means; and
   determination means for selecting one of at least two standard values in response to the condition of increase or decrease of the total value in the present cycle provided by said summing means as compared with the total value in the previous cycle stored in said memory means, said determination means comparing the total value in the present cycle with said one of at least two standard values to produce a road condition signal corresponding to a result of comparison.

2. A road condition monitoring system as set forth in claim 1, wherein said determination means selects a high standard value when the total value in the present cycle increases and selects a low standard value when the total value in the present cycle decreases, as compared with the total value in the previous cycle.

3. A road condition monitoring system as set forth in claim 2, wherein said conversion means converts said signal received from said acceleration sensor into one of three consecutive numbers in response to a magnitude of said acceleration every cycle of a predetermined time period, and wherein said determination means selects a high standard value of a large number when the total value in the present cycle increases and selects a low standard value of a small number when the total value in the present cycle decreases, as compared with the total value in the previous cycle, and said determination means compares the total value in the present cycle with said high and low standard values to produce one of two road condition signals representing a high coefficient of friction and a low coefficient of friction respectively.

4. A road condition monitoring system as set forth in claim 3, said acceleration sensor includes a pendulum rotatably mounted around an axis and a photocoupler disposed opposite to said pendulum, said pendulum being formed at the peripheral end portion thereof with a pair of slits for allowing light pass therethrough to output a signal indicating the acceleration in one of three magnitude ranges in response to the position of said slits relative to said photocoupler.

5. A road condition monitoring system comprising:
   an acceleration sensor for detecting an acceleration of a vehicle and producing a signal corresponding thereto;
   conversion means for receiving said signal from said acceleration sensor and converting said signal into one of three predetermined values in response to a magnitude of said acceleration every cycle of a predetermined time period;
   summing means for summing up said one of three predetermined values in a predetermined number of consecutive cycles and providing a total value in the last cycle thereof;
   memory means for storing the total value provided by said summing means; and
   determination means for providing a first high standard value, a first low standard value, a second high standard value higher than said first high standard value, and a second low standard value higher than said first low standard value, and determining the condition of increase or decrease of the total value in the present cycle provided by said summing means as compared with the total value in the previous cycle stored in said memory means, wherein said determination means compares the total value in the present cycle with said first high and low standard values, when the total value in the present cycle decreases, to produce a first road condition signal in case of being higher than said first high standard value, a second road condition signal in case of getting lower than said first high standard value, and a third road condition signal in case of getting lower than said first low standard value, and wherein said determination means compares the total value in the present cycle with said second high and low standard values, when said total value in the present cycle increases, to produce said first road condition signal in case of exceeding said second high standard value, said second road condition signal in case of exceeding said second low standard value, and said third road condition signal in case of being lower than said second low standard value, and produce a road condition signal determined on the basis of the total value in the previous cycle when the total value in the present cycle is the same as the total value in the previous cycle.

6. A road condition monitoring system as set forth in claim 5, wherein said conversion means converts said signal received from said acceleration sensor into one of three consecutive numbers in response to a magnitude of said acceleration every cycle of a predetermined time period, and wherein said determination means produces a signal representing high coefficient of friction as said first road condition signal, a signal representing a medium coefficient of friction as said second road condition signal, and a signal representing a low coefficient of friction as said third road condition signal.

* * * * *